US00PP13671P29

(12) United States Plant Patent
Roberson

(10) Patent No.: US PP13,671 P2
(45) Date of Patent: Mar. 18, 2003

(54) LANTANA PLANT NAMED 'ROBPATDEE'

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 10/139,960

(22) Filed: May 6, 2002

(51) Int. Cl.[7] ..... A01H 5/00

(52) U.S. Cl. ..... Plt./227

(58) Field of Search ..... Plt./227

*Primary Examiner*—Kent Bell
(74) *Attorney, Agent, or Firm*—C. A. Whealy

(57) ABSTRACT

A distinct cultivar of Lantana plant named 'Robpatdee', characterized by its upright and outwardly spreading plant habit; uniformly mounded plant form; vigorous growth habit; rapid growth rate; large leaves and long internodes; freely flowering habit; and flowers that are red purple initially opening to a pale yellow with darker yellow centers and subsequently red purple with orange centers.

2 Drawing Sheets

BOTANICAL CLASSIFICATION/CULTIVAR DESIGNATION

*Lantana camara* cultivar 'Robpatdee'.

BACKGROUND OF THE INVENTION

The present Invention relates to a new and distinct cultivar of Lantana plant, botanically known as *Lantana camara*, and hereinafter referred to by the cultivar name Robpatdee.

The new Lantana is a product of a planned breeding program conducted by the Inventor in Grain Valley, Mo. The objective of the breeding program is to create freely-flowering Lantanas with attractive flower coloration.

The new Lantana originated from a cross made by the Inventor in July, 1997 of the Lantana cultivar 'Robpathal', disclosed in U.S. Plant Pat. No. 12,063, as the female, or seed parent, with an unidentified Lantana selection as the male, or pollen parent. The new Lantana was selected as a single plant from the resulting progeny by the Inventor in a controlled environment in Grain Valley, Mo., on the basis of its vigorous growth habit and attractive flower coloration.

Asexual reproduction of the new cultivar by terminal cuttings taken in a controlled environment in Grain Valley, Mo., since January, 1999, has shown that the unique features of this new Lantana are stable and reproduced true to type in successive generations.

SUMMARY OF THE INVENTION

Plants of the cultivar Robpatdee have not been observed under all possible environmental conditions. The phenotype may vary somewhat with variations in environment and culture such as temperature and light intensity, however, any variance in genotype.

The following traits have been repeatedly observed and are determined to be the unique characteristics of 'Robpatdee'. These characteristics in combination distinguish 'Robpatdee' as a new and distinct Lantana cultivar:

1. Upright and outwardly spreading plant habit; uniformly mounded plant form.

2. Vigorous growth habit; rapid growth rate.

3. Large leaves and long internodes.

4. Fragrant foliage.

5. Freely flowering habit.

6. Flowers that are red purple initially opening to a pale yellow with darker yellow centers and subsequently red purple with orange centers.

Plants of the new Lantana are comparable to plants of the female parent, the cultivar Robpathal. In side-by-side comparisons conducted in Grain Valley, Mo., plants of the new Lantana differed from plants of the cultivar Robpathal in the following characteristics:

1. Plants of the new Lantana were more vigorous and faster growing than plants of the cultivar Robpathal.

2. Plants of the new Lantana were more upright than plants of the cultivar Robpathal.

3. Plants of the new Lantana had longer internodes than plants of the cultivar Robpathal.

4. Plants of the new Lantana and the cultivar Robpathal differed in flower coloration.

Plants of the new Lantana differ from plants of the male parent, the unidentified Lantana selection, and other Lantana cultivars known to the Inventor primarily in the new Lantana's unique combination of uniformly mounded plant habit, flower coloration, and freely-flowering habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph on the first sheet comprises a side perspective view of typical flowering plants of 'Robpatdee' grown in the landscape for about three years.

The photograph on the second sheet comprises a close-up view of typical inflorescences and leaves of 'Robpatdee'.

DETAILED BOTANICAL DESCRIPTION

In the following description, color references are made to The Royal Horticultural Society Colour Chart except where general terms of ordinary dictionary significance are used. Plants used for the description were planted in hanging basket containers after rooting and grown for about 3 months during the spring in a polyethylene-covered greenhouse in Grain Valley, Mo. During the production of the plants in the greenhouse, day temperatures were about 24° C. and night temperatures were about 18° C. Plants were finished in Keller, Tex. in an outdoor nursery from March until early May, 2002.

Botanical classification: *Lantana camara* cultivar Robpatdee.

Parentage:

*Female parent.*—*Lantana camara* cultivar Robpathal, disclosed in U.S. Plant Pat. No. 12,063.

*Male parent.*—Unidentified *Lantana camara* selection, not patented.

Propagation:

*Type cutting.*—Terminal cuttings.

*Time to initiate roots, summer.*—About 13 days at 27° C.

*Time to initiate roots, winter.*—About 15 days at 27° C.

*Time to develop roots, summer.*—About 39 days at 29° C.

*Time to develop roots, winter.*—About 46 days at 24° C.

*Root description.*—Fine, fibrous; initially glaucous white in color then becoming tan, 161D, with development.

*Rooting habit.*—Freely branching.

Plant description:

*Form.*—Flowering subshrub; upright and outwardly spreading; uniformly mounded plant form. Freely branching; two lateral branches potentially forming at every node; pinching enhances lateral branch development.

*Plant height.*—About 33 cm.

*Plant diameter.*—About 82 cm.

*Vigor.*—Vigorous, rapid growth rate.

*Lateral branches.*—Length: About 32 cm. Diameter: About 4 mm. Internode length: About 5.1 cm. Strength: Strong, but flexible. Texture: Rough, pubescent. Color: Young: 144A. Woody: Closest to 199B.

*Foliage description.*—Leaves simple, generally symmetrical and long-persisting; opposite. Length: About 8.2 cm. Width: About 5.3 cm. Shape: Ovate. Apex: Acute. Base: Obtuse with truncate tendencies. Margin: Crenate to serrate with ciliation. Texture, both surfaces: Leathery, rough, coarse; pubescent. Luster: Upper surface: Slightly glossy. Lower surface: Dull. Venation pattern: Pinnate, arcuate. Fragrance: Mint-like. Color: Young and fully expanded foliage, upper surface: 147A. Young and fully expanded foliage, lower surface: Close to 147B. Venation, upper surface: 144A to 146A. Venation, lower surface: Close to 147D. Petiole length: About 1.3 cm. Petiole diameter: About 2 mm. Petiole texture, both surfaces: Slightly pubescent. Petiole color: Upper surface: 144A to 146A. Lower surface: Close to 147D.

Flower description:

*Flower type and habit.*—Small salverform flowers arranged in axillary umbels; flowers face mostly upward or outward. Flowers self-cleaning. Very freely flowering with potentially two inflorescences per node; typically about 28 flowers per umbel.

*Natural flowering season.*—Spring until frost in the autumn; flowering continuous and consistent.

*Flower longevity on the plant.*—About one week.

*Fragrance.*—Faint, spicy, pleasant.

*Inflorescence diameter.*—About 3.6 cm.

*Inflorescence height.*—About 2.3 cm.

*Flowers.*—Appearance: Flared trumpet, corolla fused, four-parted; flowers roughly rectangular in shape. Diameter: About 1 cm by 9 mm. Corolla tube length: About 1 cm.

*Flower buds* (*before showing color*).—Length: About 4 mm. Diameter: About 4.5 mm. Shape: Roughly spherical. Color: 144A to 143A.

*Corolla.*—Arrangement/appearance: Single whorl of four petals, fused into flared trumpet. Petal length from throat: Upper and lower petals: About 5 mm. Lateral petals: About 4 mm. Petal width: Upper and lower petals: About 6 mm. Lateral petals: About 3.5 mm. Petal shape: Spatulate to somewhat orbicular. Petal apex: Rounded, acute or emarginate. Petal margin: Entire. Petal lobe texture, upper and lower surfaces: Smooth, velvety. Corolla throat and tube texture: Pubescent. Color: Petals, before opening: Close to 59A to 58A. Petal lobes, upper surface, when opening: White, close to 155D, overlain with 9A mostly towards the base; center towards throat, close to 17A. Petal lobes, lower surface, when opening: 9D to 10D. Petal lobes, upper surface, fully opened: White, close to 155D, overlain with 61A; center towards throat, close to 28A to darker than 28A; center towards throat becoming closer to 57A with subsequent development. Petal lobes, lower surface, fully opened: White, close to 155D, faintly underlain with 61A. Throat: 17A to 21A; becoming close to 155D with subsequent development. Tube: White, close to 155D, underlain with 17A; becoming close to 155D underlain with 61A with subsequent development.

*Calyx.*—Arrangement/appearance: One single calyx tube per flower. Calyx length: About 2 mm. Calyx width: About 1 mm. Apex: Two-pointed. Texture: Pubescent. Color, both surfaces: Close to 144C.

*Peduncles.*—Length: About 2.75 cm. Diameter: About 1 mm. Angle: About 45° from the stem. Strength: Flexible, but strong. Texture: Pubescent. Color: 144A.

*Pedicels.*—Not observed, flowers not stalked.

*Reproductive organs.*—Stamens: Quantity/arrangement: Four per flower, adnate to floral tube. Filament length: About 6 mm. Filament color: White, close to 155D. Anther shape: Ovoid. Anther length: Less than 1 mm. Anther color: 9A. Pollen amount: Scarce. Pollen color: Close to 17A. Pistils: Quantity: One per flower. Pistil length: About 2.5 mm. Stigma shape: Globular. Stigma color: Close to 151D. Ovary color: Close to 144A to 144B.

*Seed/fruit.*—Seed and fruit development has not been observed.

Disease/pest resistance: Plants of the new Lantana grown in the garden have been noted to be resistant to pathogens or pests common to Lantana. When grown in the greenhouse, plants of the new Lantana have been observed to be attractive to whiteflies.

Weather tolerance: Plants of the new Lantana have been observed to be very tolerant to rain and wind.

Temperature tolerance: Plants of the new Lantana have been observed to be tolerant to temperatures ranging from 0 to 38° C.

I claim:

1. A new and distinct cultivar of Lantana plant named 'Robpatdee', as illustrated and described.

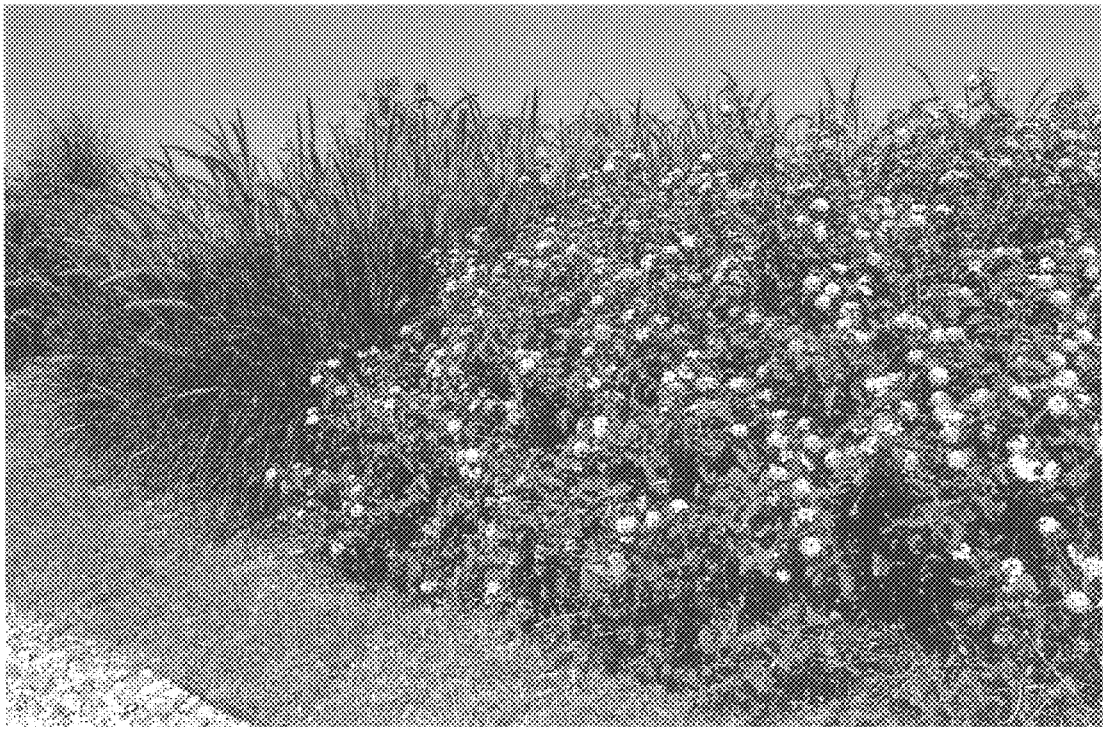

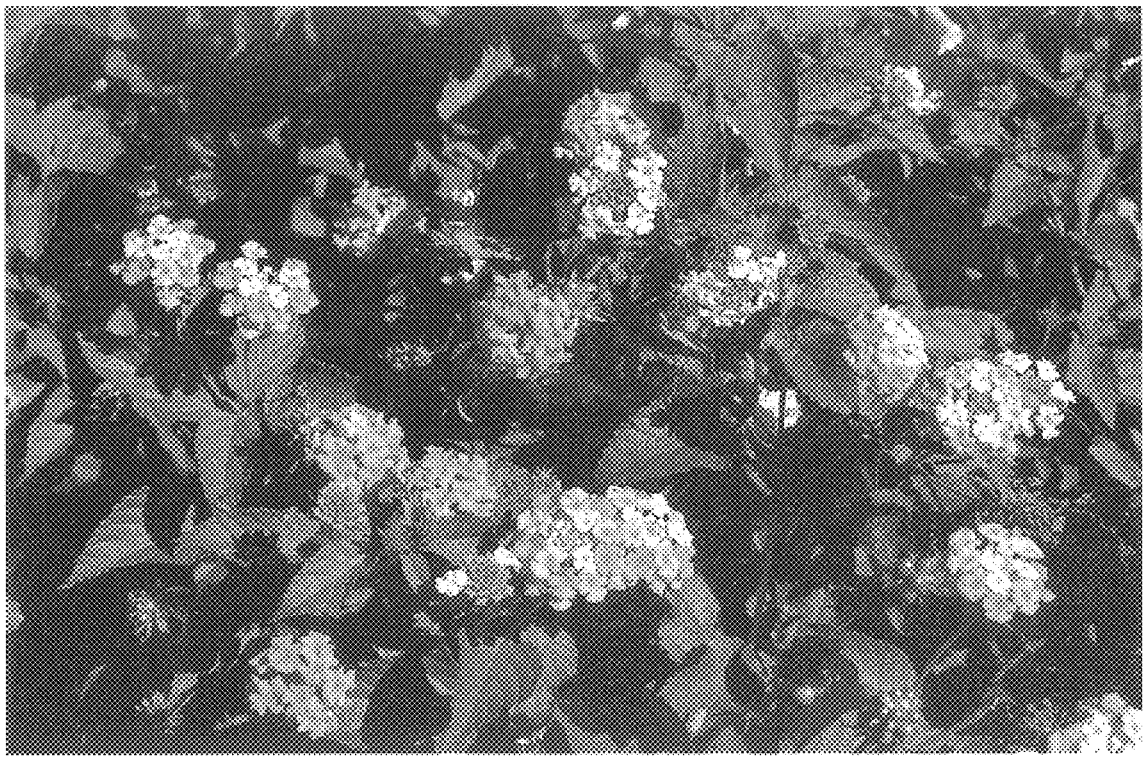

* * * * *